US00PP30007P3

(12) United States Plant Patent
McGinnis

(10) Patent No.: US PP30,007 P3
(45) Date of Patent: Dec. 25, 2018

(54) BLACK CURRANT PLANT NAMED 'STIKINE'

(50) Latin Name: ***Ribes nigrum* L.**
Varietal Denomination: Stikine

(71) Applicant: McGinnis Berry Crops Limited, Courtenay (CA)

(72) Inventor: Richard McGinnis, Courtenay (CA)

( * ) Notice: Subject to any disclaimer, the term of this patent is extended or adjusted under 35 U.S.C. 154(b) by 317 days.

(21) Appl. No.: 14/998,743

(22) Filed: Feb. 9, 2016

(65) Prior Publication Data

US 2017/0231132 P1 Aug. 10, 2017

(51) Int. Cl.
*A01H 5/08* (2018.01)

(52) U.S. Cl.
USPC ..... Plt./156
CPC ..... *A01H 5/08* (2013.01)

(58) Field of Classification Search
USPC ..... Plt./156
CPC ..... A01H 5/08
See application file for complete search history.

*Primary Examiner* — Kent L Bell
(74) *Attorney, Agent, or Firm* — Gearhart Law LLC

(57) ABSTRACT

A new and distinct cultivar of black currant (i.e. *Ribes nigrum* L.) is provided. Appealing flavor, long upright shoots, multiple racemes per bud, large fruits size and frost hardiness characterize the plant. The mid-season is ideal for North American markets due to the flavor, frost hardiness, and high yields.

4 Drawing Sheets

Genus and species: A new and distinct cultivar of black currant (i.e. *Ribes nigrum* L.) is provided.

Variety denomination: The variety denomination is 'Stikine'.

BACKGROUND OF THE EMBODIMENTS

The new black currant (*Ribes nigrum* L.) cultivar, was created as part of the planned crossbreeding program beginning in 1998. in Courtenay, British Columbia, Canada. The new cross was completed in 2005 and selected for further field trials in 2008. The female (seed) parent used was 'Zusha' ('Minaj Shmyrev' x 'Ershistaya') and the male (pollen) parent used was 'Titania' ('Altaskaya Dessertnaya' x ['Consort' x 'Kayaanin']), defined as 'Zusha' x 'Titania'. 'Titania' is the subject of U.S. Plant Pat. No. 11,439 granted Jul. 11, 2000. The patent status of 'Zusha' is unknown.

'Stikine' is the product of a 2001 cross between 'Zusha' as seed parent and 'Titania' as pollen parent. It was necessary to time the flowering as 'Zusha' flowers 7-10 days prior to 'Titania'. We used a cooler to delay flowering in 'Zusha'.

The crosses were made in a greenhouse to avoid losses due to frost. Pollen was extracted from anthers, using forceps. The anthers were placed under a heat lamp overnight. After removing the anthers from the seed parent with forceps, and with a separate set of forceps and with the aid of a magnifying visor, pollen was applied to each pistil. The pollinated flowers were covered with a bag for two weeks.

Seeds were collected from the pollinated flowers and stored in a cool place until they were planted in seed trays. The seeds were germinated in the greenhouse. Seedlings were screened for symptoms of White pine blister rust before selection. The plants were grown out for two years. Each year each plant was examined for symptoms of white pine blister rust. In 2011, each plant was evaluated for yield potential, growth habit, resistance to powdery mildew fruit size.

Trials were replicated in the following locations in Canada:

Courtenay, British Columbia
West Saanich, British Columbia
Chilliwack, British Columbia

SUMMARY OF THE EMBODIMENTS

The new cultivar is distinguished from other varieties by the following characteristics:

a. Outstanding flavor profile—the pleasant flavor expressed in the fruit of the plant is characterized by the 'Minaj Shmyrev' lineage and more fitting for the North American market than traditional black currant flavors.
b. High yields—the multiple racemes per bud and number of buds per shoot lend this variety to high flower and fruit counts per plant (FIG. 1 and FIG. 2). In replicated trials in Chilliwack, BC, the variety yielded on average 8.36 pounds of fruit per plant in comparison to Titania, which yielded 0.73 pounds on average per plant.
c. Even ripening—the mid-season variety, fully cropping a few days before 'Titania', displays even onset of ripening ideal for onetime harvesting of fruit in a commercial setting (FIG. 2).
d. Fruit size—the variety has large fruit even in comparison to other large fruit varieties such as 'Titania'. The average single berry weight for the cultivar is 0.046 ounces compared to 0.035 ounces for 'Titania'. Similarly the fifty-berry weight is 2.3 ounces compared to 1.7 ounces for 'Titania' on average.
e. Frost tolerance—the fruit of the plant has tolerance to frost as characterized by the Russian plant parent 'Zusha' during flowering in comparison to 'Titania'.
f. Disease resistance—Compared with plant parent 'Titania', 'Stikine' is more tolerant of cold conditions at time of flowering; has more upright growth habit, higher yields, somewhat larger fruit and outstanding flavor profile. Compared with plant parent 'Zusha', 'Stikine' flowers 7-9 days later.

g. Compared with 'Ben Lomond', 'Ben Alder' and 'Ben Tirran', 'Stikine' is highly resistant to white pine blister rust as is its paternal parent 'Titania'. The cultivar of interest has been asexually reproduced from hardwood cuttings in Courtenay, BC Canada. The area where the plant was discovered is the Comox Valley, BC which has mild weather conditions during most seasons.

BRIEF DESCRIPTION OF THE DRAWINGS

The appended photographs demonstrate typical specimens of the new cultivar in color and relative size as true as is reasonably possible.

DESCRIPTION OF THE PREFERRED EMBODIMENTS

Description of the Cultivar

The following is a detailed description of 3 year old plants of the new variety as observed at the trial location in Saanich, British Columbia, Canada. Colors referenced are described and notated using the Munsell® Color Charts for Plant Tissue standards.

Plant:

*Growth habit*.—Long, upright branches spread at time of fruiting due to crop weight making the growth habit high, round.

*Dimensions*.—Average plant height is 50 inches tall and 28 inches in diameter.

*Basal shoots*.—4 to 6 (without pruning)); average length of 40 inches and diameter of 0.5 inches. Mottled colored varying between 5 YR 8/2 and 5 YR 5/2 on the Munsell color chart, with medium roughness.

*Vigor*.—Strong, sturdy shoots usually erect except in over-productive seasons where fruit weight spreads the shoots. Shoots not so brittle as to break under weight.

*Roots*.—Fibrous.

Leaf buds:

*Bud frequency*.—19 buds per stem on average.

*Bud coloration*.—5 R 5/8.

*Bud appearance*.—Broad acute bud apex, 0.5 inches in length and 0.1 inches in diameter on average.

*Bud burst*.—Mar. 23, 2015.

Leaves:

*Leaf coloration*.—Upper Leaf GY 6/10; lower leaf 7.5 GY 8/6.

*Leaf appearance*.—Medium to weak glossiness on the upper side and no glossiness on the underside, palmatifid lobed leaf that is cordate in shape at the base and acute at the tip. Leaf margins are serrate.

*Leaf texture*.—Smooth but rugose.

*Leaf venation*.—Dichotomous 7.5 GY 8/8.

Figure 4:
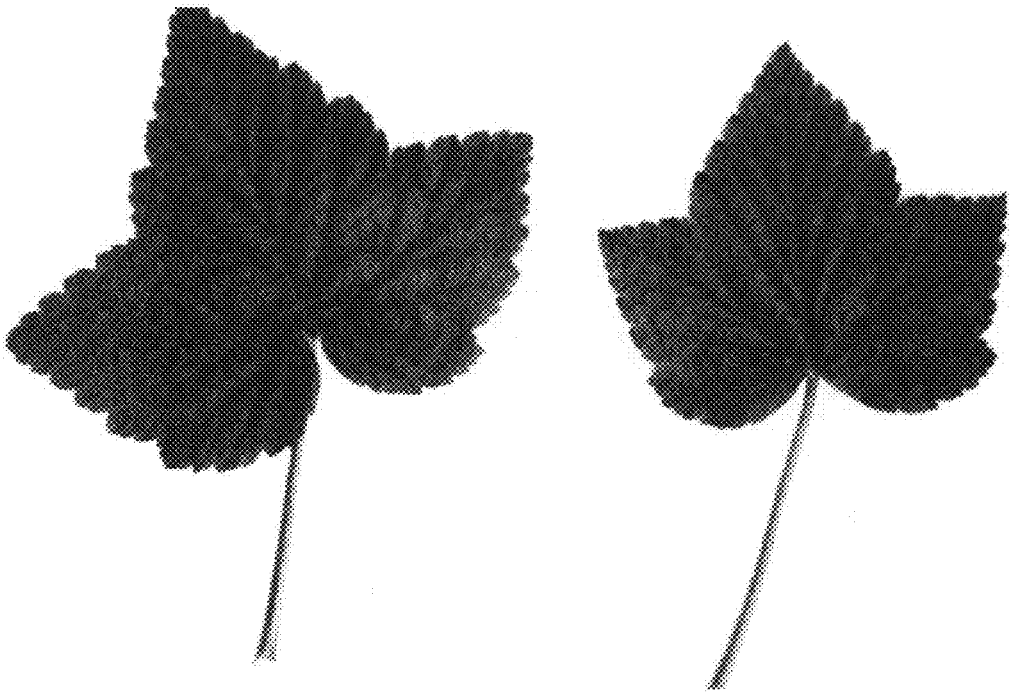
FIG. 4. Demonstration of leaf shape and relative size of new variety (right image) to 'Titania' (left image) of plant located in Courtney, Canada and at an age of 3 years. Color is not accurately represented in image due to technology limitations.

*Leaf configuration*.—In comparison to 'Titania' the base of the leaf is narrower. The terminal lobe is smaller and the rugosity is comparable in severity. See FIG. 4.

*Leaf arrangement*.—Alternating pattern; between 18 per stem on average.

*Leaf size*.—2.76 inches long and 2.90 inches wide on average.

*Petiole stem coloration*.—GY 7/8.

Bract:

*Bract coloration*.—2.5 GY 8/6 (all surfaces).

*Bract appearance*.—0.04 inches in length, simple overall structure with entire margins, acute tip and a clasping base.

*Bract texture*.—Smooth (all surfaces).

Flower bud:

*Bud appearance*.—Narrow acute apex, 0.55 inches in length and 0.2 inches in diameter.

*Bud coloration*.—7.5 GY 8/4.

Flowers:

*Bud color*.—5R 5/8.

*Flowering date*.—Apr. 25, 2015 Flowering period — April 25 through May 9.

*Flower coloration*.—5RP 6/10.

*Flower appearance*.—0.5 inches in length and 0.3 inches in diameter, the flowers are bell-shaped to funnel-shaped when in full bloom.

*Flower racemes*.—Long, several per node, frequent.

*Flower frequency*.—Consistently several racemes per bud with 8-12 flowers per raceme.

*Petal frequency*.—5 per flower.

*Petal appearance*.—Linear shape, rounded apex, entire margins, sessile base. 0.3 inches in length and 0.1 inches in diameter, neither surface is waxy, but smooth.

*Petal texture*.—Slightly downy (both surfaces).

*Sepal to petal frequency*.—1 sepal to 1 petal.

*Sepal appearance*.—Linear shape, rounded apex, entire margins, sessile base. 0.55 inches in length and 0.1 inches in diameter, neither surface is waxy, but smooth.

*Sepal coloration*.—5 R 5/8.

*Anther appearance*.—5 Y 8/8.

*Ovary appearance*.—2.5 GY 8/8.

*Pedicle appearance*.—10 R 7/4, 0.3 inches in length.

*Peduncle appearance*.—10 R 7/4, 1.6 inches in length.

Fruit:

*Size*.—Large sized fruit (notably larger than 'Ben Alder' and large in comparison to 'Titania'.) The average single berry weight is 0.046 ounces.

*Taste*.—Pleasant, sweet, unique, mildly acidic palatable taste.

*Configuration*.—Round.

*Consistency*.—Firm, medium skin thickness, smooth texture, and minimal waxiness.

Figure 1:
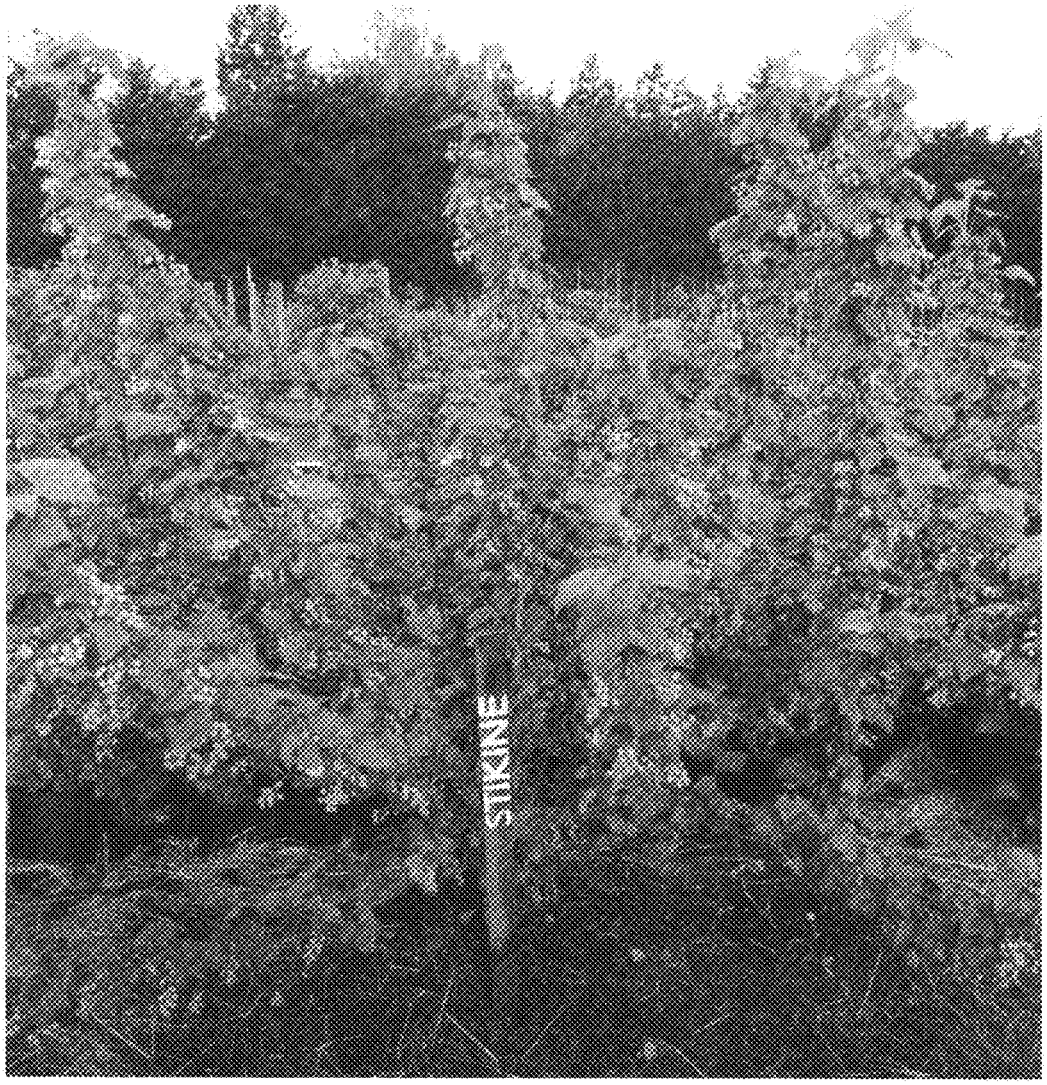
FIG. 1. Demonstration of overall raceme/flower frequency and distribution of plant located in Saanich, Canada and at an age of 3 years.
Figure 2:
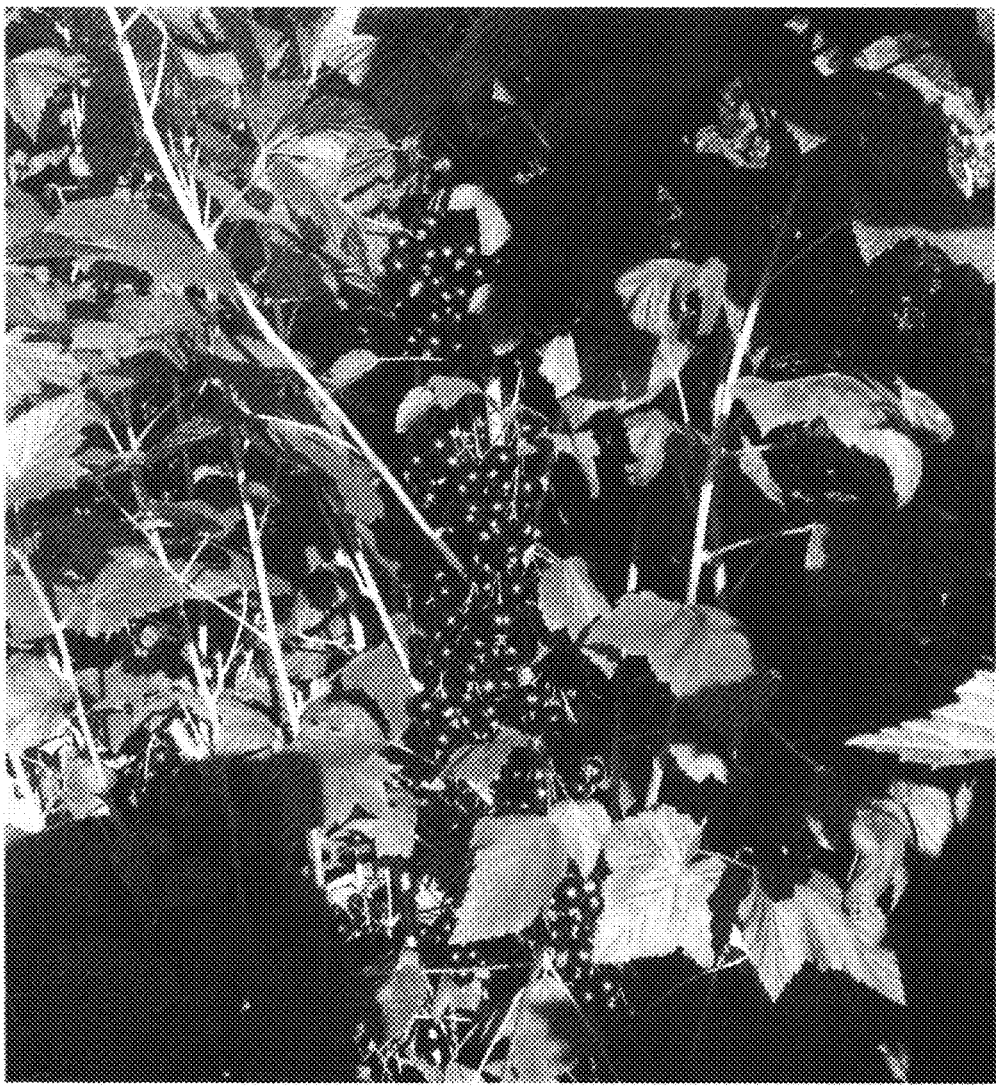
FIG. 2. Demonstration of fruit color, even ripeness, yield, and distribution of plant located in Saanich, Canada and at an age of 3 years.
Figure 3:
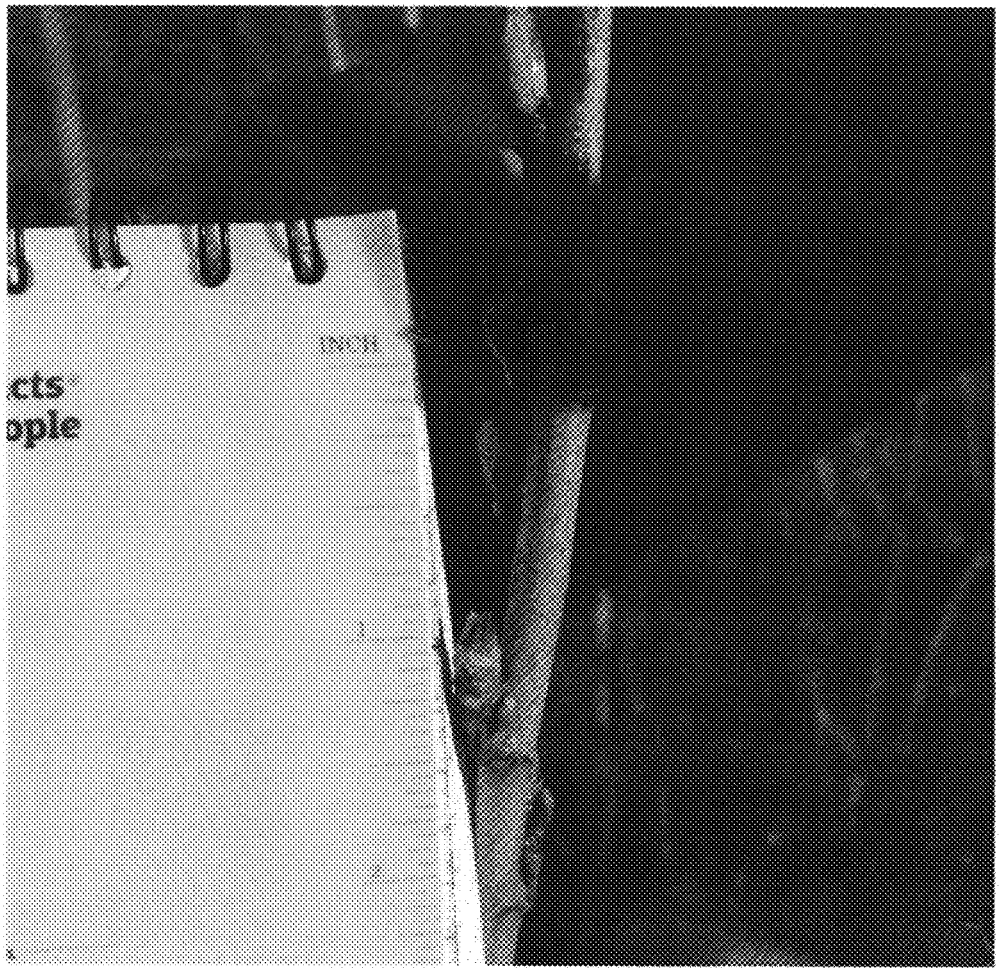
FIG. 3. Demonstration of bud size, shape, color, and spacing of plant located in Saanich, Canada and at an age of 3 years.

*Appearance*.—Medium glossiness, black when ripe 5 RP 3/2. Attractive and presented in dense sections with uniform berry size and color within a section. See FIG. 2.

*Fruit ripening*.—Even.

*Yields*.—Multiple racemes per bud, high number of buds per shoot (thus high flower and fruit counts). Yields on average 8.36 pounds of fruit per plant. Approximately 22 berries per cluster.

*Management and harvesting*.—The variety is suited for machine-harvest as evident by the upright growth and even ripening of fruit. Additionally, the plants are suitable for hand-harvest with the large, firm fruit and multiple tight racemes per bud for quick harvest of many fruit.

*Management and harvesting*.—Suitable for machine harvest due to even ripening and growth habit. Also suitable for hand picking due to easy to pick groups of berries (racemes).

*Market*.—Marketable for both commercial and domestic production due to the flexibility in harvest methods (hand or machine). The sweeter, less acidic taste lends itself for consumption by the North American market both in fresh fruit and processed form. Frost hardiness, white pine blister rust immunity, and mildew resistance allow for robust growing conditions.

Disease and pest resistance: The cultivar is immune to white pine blister rust (*Cronartium ribicola* Fisch.) in British Columbia (a characteristic of parent plant, 'Titania'). The cultivar is resistant to powdery mildew and *Septoria* leaf spot (*Septoria ribis* Desm.)

Resistance to cold: Flowers display frost hardiness compared to its parent plant, 'Titania'.

What is claimed is:

1. A new and distinct variety of Black Currant plant as illustrated and described.

* * * * *